United States Patent
Chandel et al.

(10) Patent No.: US 12,367,983 B2
(45) Date of Patent: Jul. 22, 2025

(54) METHOD AND A SYSTEM FOR REAL TIME ANALYSIS OF RANGE OF MOTION (ROM)

(71) Applicant: Tata Consultancy Services Limited, Mumbai (IN)

(72) Inventors: Vivek Chandel, Gurgaon (IN); Avik Ghose, Kolkata (IN); Murali Poduval, Mumbai (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 296 days.

(21) Appl. No.: 17/982,812

(22) Filed: Nov. 8, 2022

(65) Prior Publication Data

US 2023/0154621 A1 May 18, 2023

(30) Foreign Application Priority Data

Nov. 13, 2021 (IN) .............................. 202121052132

(51) Int. Cl.
*G01C 25/00* (2006.01)
*G16H 20/30* (2018.01)
*G16H 50/30* (2018.01)

(52) U.S. Cl.
CPC ............. *G16H 50/30* (2018.01); *G16H 20/30* (2018.01)

(58) Field of Classification Search
CPC .................................................... H04W 4/023
See application file for complete search history.

(56) References Cited

U.S. PATENT DOCUMENTS

2011/0190595 A1* 8/2011 Bennett .................... A61B 1/05
600/300
2014/0052463 A1* 2/2014 Cashman ........... G06Q 10/1095
705/2
(Continued)

FOREIGN PATENT DOCUMENTS

CN 112603295 A 4/2021
DE 102022203454 A1 * 10/2023

OTHER PUBLICATIONS

Allseits et al., "A Novel Method for Estimating Knee Angle Using Two Leg-Mounted Gyroscopes for Continuous Monitoring with Mobile Health Devices," Sensors, 18(2759) (2018).
(Continued)

Primary Examiner — Reginald R Reyes
(74) Attorney, Agent, or Firm — Finnegan, Henderson, Farabow, Garrett & Dunner, LLP

(57) ABSTRACT

This disclosure relates generally to real time analysis of range of motion (ROM), wherein ROM is a measurement of movement around a specific joint or body part. The existing techniques for ROM fail for measurements made in certain planes and are not very effective for ROM measurements for extremely slow and very fast movements. The disclosed provides a real time analysis of ROM based on computation of range of motion (ROM) of a joint and a set of ROM parameters using a gyroscope. The gyroscope collects data from a subject at pre-defined neutral position of the subject as well as a pre-defined rotation movement of a joint of the subject. The received data is corrected for bias and processed at real time to analyze the ROM by computing range of motion (ROM) of a joint and a set of ROM parameters.

17 Claims, 12 Drawing Sheets

(56) References Cited

U.S. PATENT DOCUMENTS

| | | | | |
|---|---|---|---|---|
| 2015/0257682 A1* | 9/2015 | Hansen | ............... | A61B 5/1121 |
| | | | | 382/103 |
| 2017/0173262 A1* | 6/2017 | Veltz | ...................... | G16H 20/17 |
| 2018/0144101 A1* | 5/2018 | Bitran | .................... | G16H 50/20 |
| 2019/0390976 A1* | 12/2019 | Anderson | ............... | G06F 3/013 |

OTHER PUBLICATIONS

Dejnabadi et al., "A New Approach to Accurate Measurement of Uniaxial Joint Angles Based on a Combination of Accelerometers and Gyroscopes," IEEE Transactions on Biomedical Engineering, 52(8) (2005).

Olsson et al., "Joint axis estimation for fast and slow movements using weighted gyroscope and acceleration constraints," (2019).

Qi et al., "GonioSense: A Wearable-Based Range of Motion Sensing and Measurement System for Body Joints," (2016).

\* cited by examiner

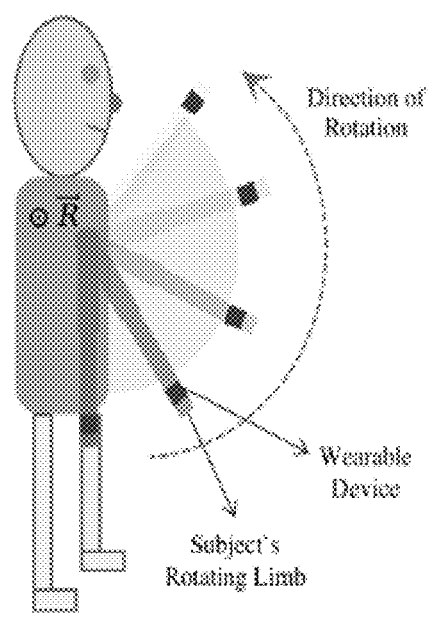 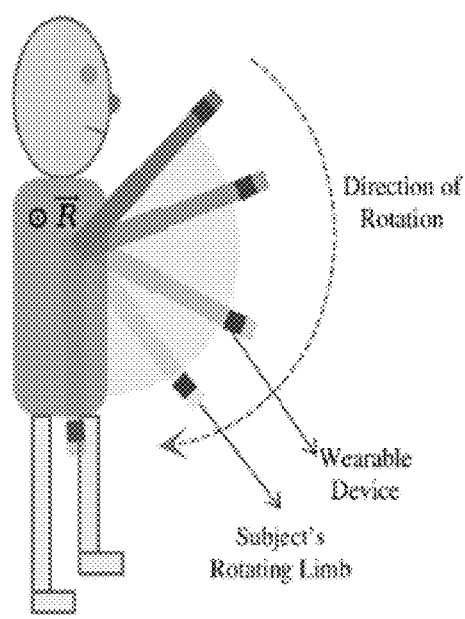
FIG. 5A                                   FIG. 5B

METHOD AND A SYSTEM FOR REAL TIME ANALYSIS OF RANGE OF MOTION (ROM)

PRIORITY CLAIM

This U.S. patent application claims priority under 35 U.S.C. § 119 to: India Application No. 202121052132, filed on Nov. 13, 2021. The entire contents of the aforementioned application are incorporated herein by reference.

TECHNICAL FIELD

The disclosure herein generally relates to the field of measurement of Range of motion (ROM), and, more particularly, to a method and a system for real time analysis of range of motion.

BACKGROUND

Range of motion (ROM) is a measurement of the amount of movement around a specific joint or a body part. The ROM is commonly measured during a physical therapy evaluation or during a course of treatment, and especially in physical examination of patients with musculoskeletal ailments, as its longitudinal assessment can help track the trajectory of recovery of the patient.

Medical grade goniometers are widely used for the purpose of ROM measurement, however goniometer-based measurement which is a manual measurement requires personal presence of a medical expert especially in passive goniometry. Further, numerous solutions have been proposed to enable digital ROM estimation using smart wearables with embedded inertial sensors for ROM measurements, wherein the smart wearables use fused information from accelerometers and gyroscopes. Although smart wearables cover a wide variety of ROM measurements, the smart wearables fail for measurements made in certain planes and require sensor specific calibration.

In addition, most of the existing state-of-art techniques can address a minimum rotation speed or ROM of over 100 deg/sec, whereas in clinical settings, speed of ROM measurements can go as low as 10 deg/sec. Hence, inertial measurement during both extremely slow and very fast movements is challenging and translates to higher manifestation of error in sensor outputs. Hence there is a requirement for a technique that can work across planes and can also address both extremely slow and very fast movements.

SUMMARY

Embodiments of the present disclosure present technological improvements as solutions to one or more of the above-mentioned technical problems recognized by the inventors in conventional systems. For example, in one embodiment, a method for real time analysis of ROM is provided. The system includes a memory storing instructions, one or more communication interfaces, and one or more hardware processors coupled to the memory via the one or more communication interfaces, wherein the one or more hardware processors are configured by the instructions to receiving a first set of gyroscope data from a subject, using a wearable device at a pre-defined neutral position of the subject, wherein the first set of gyroscope data is associated with a joint rotation of the subject at the pre-defined neutral position of the subject. The system is further configured for computing a set of bias correction parameters from the first set of gyroscope data using a static bias parameter, wherein the static bias parameter is computed from the first set of gyroscope data in a first pre-defined window and the set of bias correction parameters includes a plurality of bias corrected first set of gyroscope data and a plurality of sample angles. The system is further configured for receiving a second set of gyroscope data from the subject, using the wearable device at a pre-defined rotation movement of a joint of the subject, wherein the second set of gyroscope data is associated with the joint rotation of the subject at the pre-defined rotation movement of the joint. The system is further configured for obtaining a bias corrected second set of gyroscope data for the second set of gyroscope data using the set of bias correction parameters. The system is further configured for validating the bias corrected second set of gyroscope data as one of a valid session or an invalid session based on a deviation angle and a pre-defined delta angle, wherein the deviation angle is computed using a reference rotation axis and a rotation axis, where the reference rotation axis and the rotation axis is estimated in a second pre-defined window based on the plurality of sample angles. The system is further configured for computing range of motion (ROM) of a joint and a set of ROM parameters if the validated bias corrected second set of gyroscope data is the valid session, wherein the computing the ROM comprises: computing a real-time cumulative angle for each of the plurality of bias corrected second set of gyroscope data to obtain a plurality of the real-time cumulative angle using the plurality of sample angles, the deviation angle and the pre-defined delta angle, computing the joint ROM using the plurality of real-time cumulative angle, wherein the ROM is computed using a minimum real-time cumulative angle and a maximum real-time cumulative angle from the plurality of real-time cumulative angle and computing the set of ROM parameters, wherein the set of ROM parameters includes a speed of rotation, and a session validity score using the plurality of sample angles, a pre-defined delta angle and the deviation angle.

In another aspect, a method for real time analysis of ROM is provided. The method includes receiving a first set of gyroscope data from a subject using a wearable device at a pre-defined neutral position of the subject, wherein the first set of gyroscope data is associated with a joint rotation of the subject at the pre-defined neutral position of the subject. The method further includes computing a set of bias correction parameters from the first set of gyroscope data using a static bias parameter, wherein the static bias parameter is computed from the first set of gyroscope data in a first pre-defined window and the set of bias correction parameters includes a plurality of bias corrected first set of gyroscope data and a plurality of sample angles. The method further includes receiving a second set of gyroscope data from the subject, using the wearable device at a pre-defined rotation movement of a joint of the subject, wherein the second set of gyroscope data is associated with the joint rotation of the subject at the pre-defined rotation movement of the joint. The method further includes obtaining a bias corrected second set of gyroscope data for the second set of gyroscope data using the set of bias correction parameters. The method further includes validating the bias corrected second set of gyroscope data as one of a valid session or an invalid session based on a deviation angle and a pre-defined delta angle, wherein the deviation angle is computed using a reference rotation axis and a rotation axis, where the reference rotation axis and the rotation axis is estimated in a second pre-defined window based on the plurality of sample angles. The method further includes computing range of motion (ROM)

of a joint and a set of ROM parameters if the validated bias corrected second set of gyroscope data is the valid session, wherein the computing the ROM comprises: computing a real-time cumulative angle for each of the plurality of bias corrected second set of gyroscope data to obtain a plurality of the real-time cumulative angle using the plurality of sample angles, the deviation angle and the pre-defined delta angle, computing the joint ROM using the plurality of real-time cumulative angle, wherein the ROM is computed using a minimum real-time cumulative angle and a maximum real-time cumulative angle from the plurality of real-time cumulative angle; and computing the set of ROM parameters, wherein the set of ROM parameters includes a speed of rotation, and a session validity score using the plurality of sample angles, a pre-defined delta angle and the deviation angle.

In yet another aspect, a non-transitory computer readable medium for real time analysis of ROM is provided. The program includes receiving a first set of gyroscope data from a subject using a wearable device at a pre-defined neutral position of the subject, wherein the first set of gyroscope data is associated with a joint rotation of the subject at the pre-defined neutral position of the subject. The program further includes computing a set of bias correction parameters from the first set of gyroscope data using a static bias parameter, wherein the static bias parameter is computed from the first set of gyroscope data in a first pre-defined window and the set of bias correction parameters includes a plurality of bias corrected first set of gyroscope data and a plurality of sample angles. The program further includes receiving a second set of gyroscope data from the subject, using the wearable device at a pre-defined rotation movement of a joint of the subject, wherein the second set of gyroscope data is associated with the joint rotation of the subject at the pre-defined rotation movement of the joint. The program further includes obtaining a bias corrected second set of gyroscope data for the second set of gyroscope data using the set of bias correction parameters. The program further includes validating the bias corrected second set of gyroscope data as one of a valid session or an invalid session based on a deviation angle and a pre-defined delta angle, wherein the deviation angle is computed using a reference rotation axis and a rotation axis, where the reference rotation axis and the rotation axis is estimated in a second pre-defined window based on the plurality of sample angles. The program further includes computing range of motion (ROM) of a joint and a set of ROM parameters if the validated bias corrected second set of gyroscope data is the valid session, wherein the computing the ROM comprises: computing a real-time cumulative angle for each of the plurality of bias corrected second set of gyroscope data to obtain a plurality of the real-time cumulative angle using the plurality of sample angles, the deviation angle and the pre-defined delta angle, computing the joint ROM using the plurality of real-time cumulative angle, wherein the ROM is computed using a minimum real-time cumulative angle and a maximum real-time cumulative angle from the plurality of real-time cumulative angle; and computing the set of ROM parameters, wherein the set of ROM parameters includes a speed of rotation, and a session validity score using the plurality of sample angles, a pre-defined delta angle and the deviation angle.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 5A and FIG. 5B illustrates example scenario for a pre-defined rotation movement for an arm joint movement, wherein FIG. 5A illustrates an upward movement of the arm joint and the FIG. 5B illustrates a downward movement of the arm joint in accordance with some embodiments of the present disclosure.

DETAILED DESCRIPTION

Figure 1:
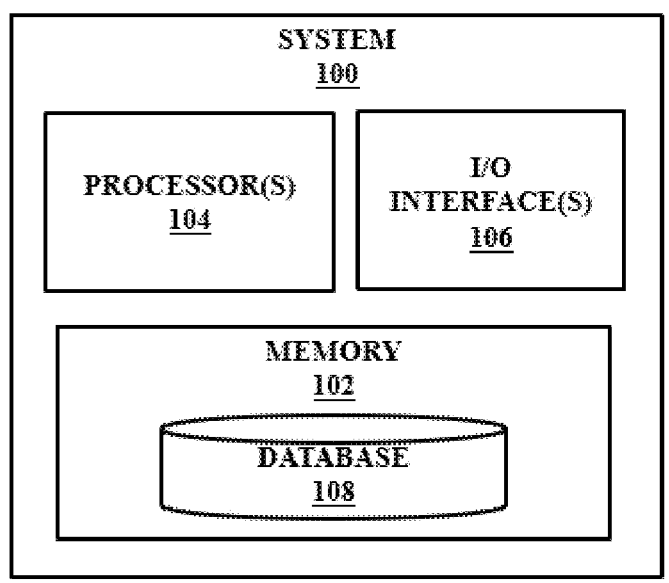
FIG. 1 illustrates a block diagram of a system for real time analysis of ROM according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Referring now to the drawings, and more particularly to FIG. 1 through FIG. 7C, where similar reference characters denote corresponding features consistently throughout the figures, there are shown preferred embodiments and these embodiments are described in the context of the following exemplary system and/or method.

FIG. 1 is a functional block diagram of a system 100 for real time analysis of ROM in accordance with some embodiments of the present disclosure.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100 with one or more hardware processors is configured to execute functions of one or more functional blocks of the system 100.

Referring to the components of the system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 is configured to fetch and execute computer-readable instructions stored in the memory 102. In an embodiment, the system 100 can be implemented in a variety of computing systems including laptop computers, notebooks, hand-held devices such as mobile phones, workstations, mainframe computers, servers, a network cloud and the like.

The I/O interface(s) 106 can include a variety of software and hardware interfaces, for example, a web interface, a graphical user interface, a touch user interface (TUI) and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server.

The memory 102 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes.

Further, the memory 102 may include a database 108 configured to include information regarding historic data associated the breathing analysis. The memory 102 may comprise information pertaining to input(s)/output(s) of each step performed by the processor(s) 104 of the system 100 and methods of the present disclosure. In an embodiment, the database 108 may be external (not shown) to the system 100 and coupled to the system via the I/O interface 106.

Figure 2:
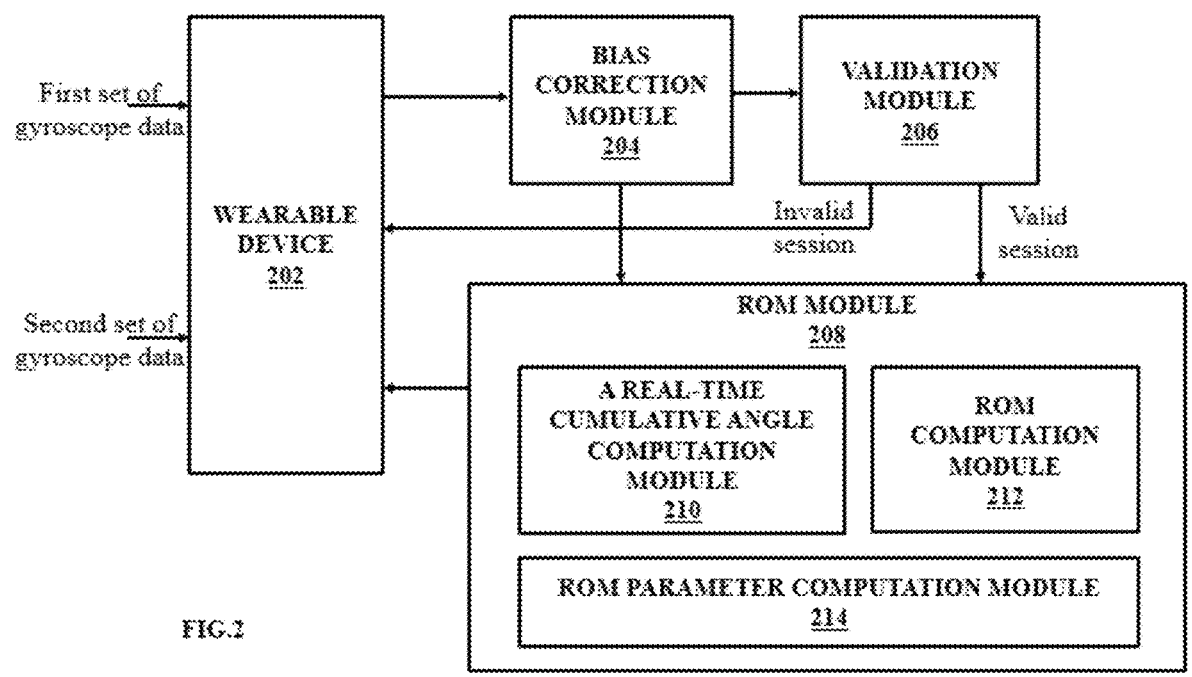
FIG. 2 is a functional block diagram of a system for real time analysis of ROM according to some embodiments of the present disclosure.
Figure 3A:
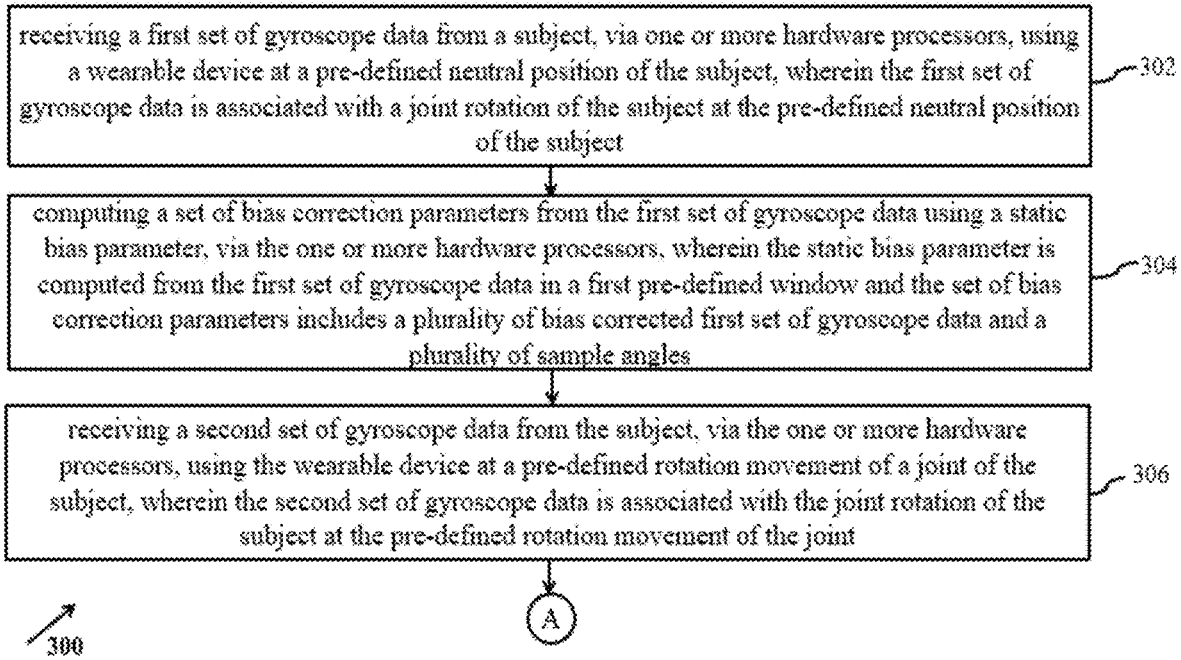
FIG. 3A, FIG. 3B and FIG. 3C is a flow diagram illustrating a method 300 for real time analysis of ROM in accordance with some embodiments of the present disclosure.
Figure 3B:
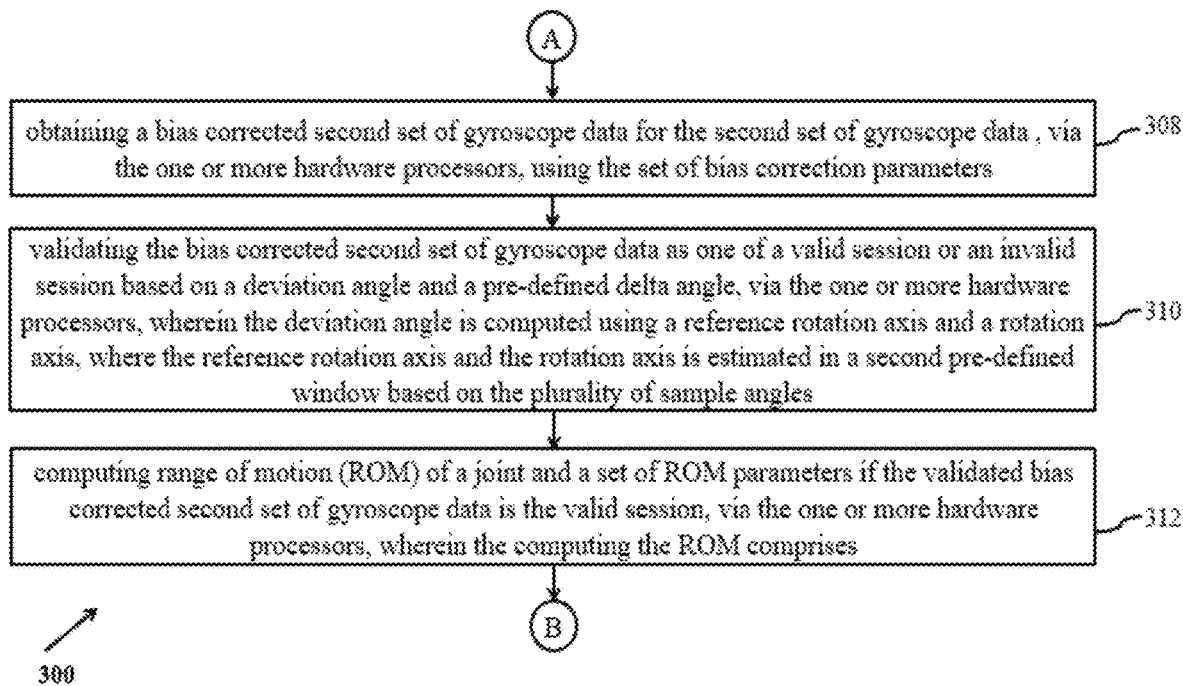
Figure 3C:
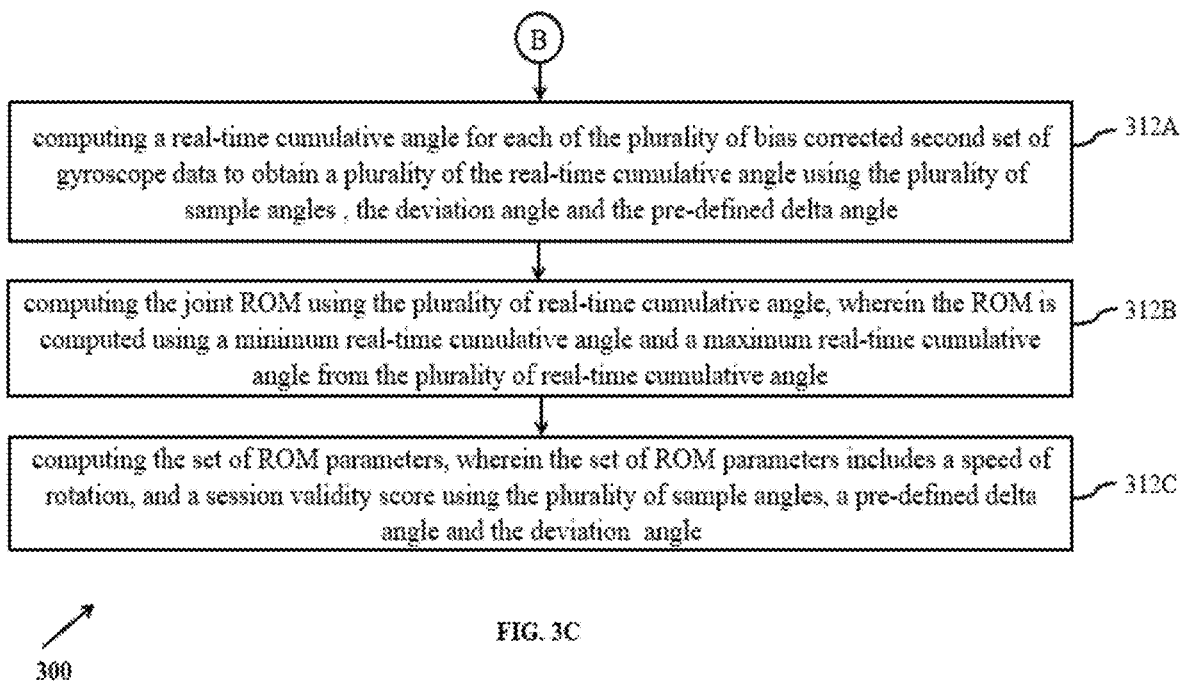

Functions of the components of system 100 are explained in conjunction with functional overview of the system 100 in FIG. 2 and flow diagram of FIGS. 3A,3B and 3C for real time analysis of ROM.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

FIG. 2 is an example functional block diagram of the various modules of the system of FIG. 1, in accordance with some embodiments of the present disclosure. As depicted in the architecture, the FIG. 2 illustrates the functions of the modules of the system 100 that includes for real time analysis of ROM.

The system 100 for real time analysis of ROM is configured to receive a first set of gyroscope data from a subject, via one or more hardware processors using a wearable device 202. The first set of gyroscope data is associated with a joint rotation of the subject at the pre-defined neutral position of the subject. The first set of gyroscope data is received at a pre-defined neutral position of the subject.

The wearable device 202 is also configured to receive a second set of gyroscope data from the subject. The second set of gyroscope data is associated with the joint rotation of the subject at the pre-defined rotation movement of the joint. The second set of gyroscope data is received at a pre-defined rotation movement of the joint of the subject.

The system 100 further comprises a bias correction module 204 configured to compute a set of bias correction parameters. The set of bias correction parameters includes a plurality of bias corrected first set of gyroscope data and a plurality of sample angles ($\alpha$). The set of bias correction parameters are computed from the first set of gyroscope data using a static bias parameter. The static bias parameter is computed from the first set of gyroscope data in a first pre-defined window.

The bias correction module 204 is also configured to obtain a bias corrected second set of gyroscope data for the second set of gyroscope data. The bias corrected second set of gyroscope data is obtained using the set of bias correction parameters computed during the first pre-defined window.

The system 100 further comprises a validation module 206 configured to validate the bias corrected second set of gyroscope data as one of a valid session or an invalid session. The validation is performed based on a deviation angle ($\phi$) and a pre-defined delta angle ($\delta$). The deviation angle is computed using a reference rotation axis ($\vec{R}$) and a rotation axis ($\vec{V}$). The reference rotation axis ($\vec{R}$) and the rotation axis ($\vec{V}$) is estimated in a second pre-defined window based on the plurality of sample angles ($\alpha$).

The system 100 further comprises a ROM module 208 configured to compute range of motion (ROM) of the joint and a set of ROM parameters if the validated bias corrected second set of gyroscope data is the valid session. The range of motion (ROM) of a joint and a set of ROM parameters is computed in the ROM module 208 using the modules within the ROM module 208 that includes a real-time cumulative angle computation module 210, a ROM computation module 212, a ROM parameter calculation module 214.

The real-time cumulative angle module 210 in the ROM module 208 is configured for computing a real-time cumulative angle ($C_i$) for each of the plurality of bias corrected second set of gyroscope data to obtain a plurality of the real-time cumulative angle (C). The real-time cumulative angle ($C_i$) is computed using the plurality of sample angles ($\alpha$), the deviation angle (($\alpha$) and the pre-defined delta angle ($\delta$).

The ROM computation module 212 in the ROM module 208 is configured for computing the joint ROM using the plurality of real-time cumulative angle (C). The ROM is computed using a minimum real-time cumulative angle (C) and a maximum real-time cumulative angle (C) from the plurality of real-time cumulative angle (C).

The ROM parameter module 214 in the ROM module 208 is configured for computing the set of ROM parameters. The set of ROM parameters includes a speed of rotation ($\omega$), and a session validity score ($\lambda$) using the plurality of sample angles ($\alpha$), a pre-defined delta angle ($\delta$) and the deviation angle ($\phi$).

The various modules of the system 100 and the functional blocks in FIG. 2 are configured for usage monitoring of equipment using a set of sensors are implemented as at least one of a logically self-contained part of a software program, a self-contained hardware component, and/or, a self-contained hardware component with a logically self-contained part of a software program embedded into each of the hardware component that when executed perform the above method described herein.

Functions of the components of the system 100 are explained in conjunction with functional modules of the system 100 stored in the memory 102 and further explained in conjunction with flow diagram of FIGS. 3A, 3B and 3C. The FIGS. 3A, 3B and 3C with reference to FIG. 1, is an exemplary flow diagram illustrating a method 300 for real time analysis of ROM using the system 100 of FIG. 1 according to an embodiment of the present disclosure. The joint ROM is calculated for a bi-directional rotational movement of joints of the subject, wherein the bi-directional rotational movement of joints comprise of limbs movement including an abduction-adduction, an extension-flexion and an internal-external rotation. The disclosed technique for estimation of ROM includes but not limited to, shoulder, elbow, knee and hip joints. Further during estimation of ROM for one pair of opposite rotation (example scenario: abduction/adduction) of the joint, it can be assumed that the plane of rotation stays approximately the same throughout the rotational movement.

The steps of the method 300 of the present disclosure will now be explained with reference to the components of the system (100) for real time analysis of ROM and the modules (202-214) as depicted in FIG. 2 and the flow diagrams as depicted in FIGS. 3A, 3B and 3C. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

At step 302 of the method 300, the first set of gyroscope data is received from the subject using the wearable device 202. The first set of gyroscope data is associated with a joint rotation of the subject at the pre-defined neutral position of the subject. The first set of gyroscope data is received at a pre-defined neutral position of the subject.

In an embodiment, the wearable device 202 comprises at least a 3-axis gyroscope sensor. The gyroscope sensor is configured to receive the first set of gyroscope data at a pre-determined rate as a plurality of data samples. In an example scenario, the typical pre-determined rate is set at 200 samples per second. Every data sample can be represented as a 4-tuple as shown below:

$$S_i = \{t_i, x_i, y_i, z_i\}. \quad (1)$$

wherein, $t_i$ represents a timestamp associated with the plurality of data samples of the first set of gyroscope data;
$x_i$ represents a rotational speed around X-Axis;
$y_i$ represents a rotational speed around Y-Axis; and
$z_i$ represents a rotational speed around X-Axis.

The pre-defined neutral position of the subject is the neutral position of the subject from where the range of motion (ROM) calculations start. In an example scenario, A pre-defined neutral position is defined for every well-known ROM rotation marking the starting position of the limb for a ROM estimation session from where the joint can be rotated in either direction for ROM estimation (example: abducting in one direction, adducting in another direction). In an example scenario, for abduction/adduction, and extension/flexion of a shoulder, the pre-defined neutral position may be defined as the arm pointing downwards with palm facing the body, wherein a starting position can also be selected by a medical specialist as per their preference according to the requirement of their analysis.

In one embodiment, upon receiving the first set of gyroscope data at the wearable device 202, the first set of gyroscope data can be processed for computation of ROM within the wearable device 202 using the modules (204 to 214). In another embodiment, the processing of the first set of gyroscope data for computation of ROM can run on a separate host system wirelessly using the modules (204 to 214). Further the computed ROM can be displayed in real time on a screen which is available with the separate host system, or in another embodiment, the computation of ROM can be displayed on the wearable device 202. Hence for computation of ROM can be performed within the wearable device 202 or on a separate system based on a user requirement.

At step 304 of the method 300, a set of bias correction parameters is computed in the bias correction module 204. The set of bias correction parameters includes a plurality of bias corrected first set of gyroscope data and a plurality of sample angles ($\alpha$). The set of bias correction parameters are computed from the first set of gyroscope data using a static bias parameter. The static bias parameter is computed from the first set of gyroscope data in a first pre-defined window.

As the first set of gyroscope data is received at the gyroscope of the wearable device 202 in the pre-defined neutral position of the subject The subject is directed to keep their limb (for which joint ROM is computed) in the pre-defined neutral position for a pre-determined duration, $T_s$, which is typically 2 seconds, which is when the range of motion (ROM) calculations start. The first set of gyroscope data is processed in the first pre-defined window for $T_s$ seconds. The first pre-defined window is defined based on a standard deviation of the first set of gyroscope data and a first pre-defined threshold ($C_L$) on the standard deviation of the first set of gyroscope data for a "$m^{th}$" data sample of the first set of gyroscope data from a plurality of "k" plurality of data samples of the first set of gyroscope data. The first pre-defined threshold ($C_L$) represents a threshold on the standard deviation of the first set of gyroscope data, with a typical value of 0.01 degrees per second. The first pre-defined window is defined as shown below:

$$\text{std}\{x_i : i \leq i < m+k\} < C_L$$

$$\text{std}\{y_i : i \leq i < m+k\} < C_L$$

$$\text{std}\{z_i : i \leq i < m+k\} < C_L \quad (2)$$

Figure 4:
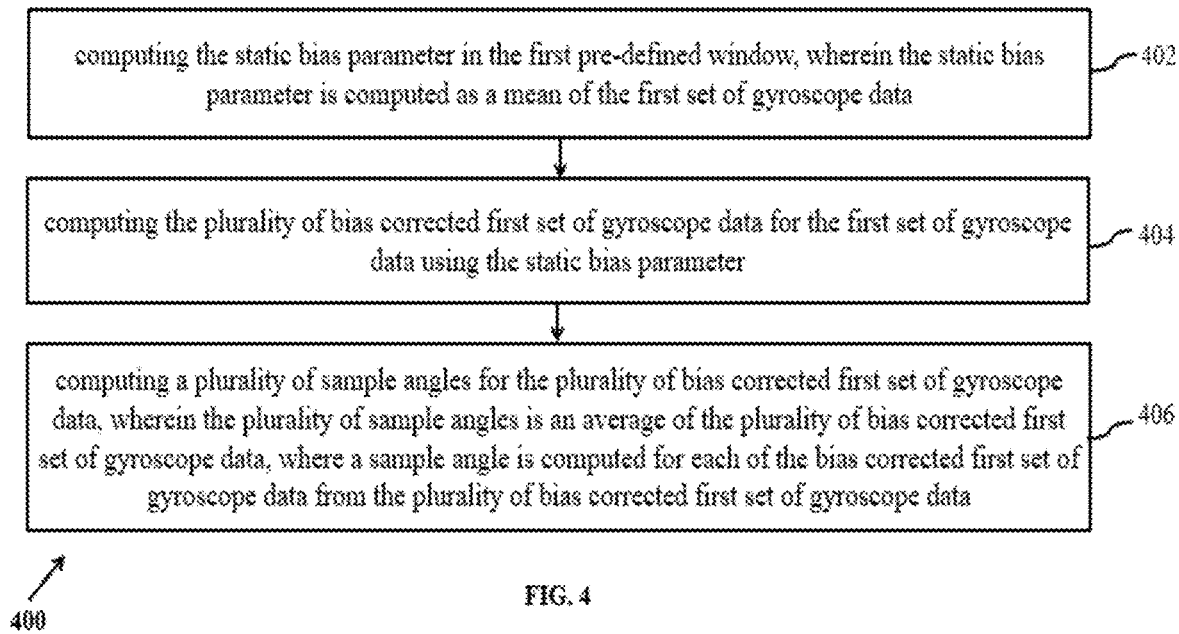
FIG. 4 is a flow diagram illustrating method for computing a set of bias correction parameters for real time analysis of ROM in accordance with some embodiments of the present disclosure.

In an embodiment, the process of computing a set of bias correction parameters is explained using the flowchart 400 of FIG. 4. The process of computing a set of bias correction parameters comprises:

At step 402 of the method 400, the static bias parameter in the first pre-defined window is computed. The static bias parameter is computed as a mean of the first set of gyroscope data.

In an embodiment, the static bias parameter is computed as a mean of the first set of gyroscope data taken independently in all the three axes of the gyroscope and can be represented as $B_x$, $B_y$, $B_z$. The static bias parameter is expressed as shown below:

$$B_x = \frac{\sum_{k=m}^{m+k-1} x_i}{k}, B_y = \frac{\sum_{k=m}^{m+k-1} y_i}{k}, B_z = \frac{\sum_{k=m}^{m+k-1} z_i}{k} \quad (3)$$

At step 404 of the method 400, the plurality of bias corrected first set of gyroscope data is computed for the first set of gyroscope data. The plurality of bias corrected first set of gyroscope data is computed using the static bias parameter.

In an embodiment, all the first set of gyroscope data lying between, i>m+k−1, plurality of bias corrected first set of gyroscope data is computed as follows:

$$S_i = \{t_i, X_i, Y_i, Z_i\} \quad (4)$$

where,
$X_i = x_i - B_x$,
$Y_i = y_i - B_y$, and
$Z_i = z_i - B_z$.

Hence the plurality of bias corrected first set of gyroscope data is computed for the first set of gyroscope data bias correction for a particular data sample can be performed by subtracting the calculated static bias parameter from the actual raw sample value.

At step 406 of the method 400, a plurality of sample angles ($\alpha$) is computed for the plurality of bias corrected first set of gyroscope data. The sample angle is computed for each of the bias corrected first set of gyroscope data from the plurality of bias corrected first set of gyroscope data.

The plurality of sample angles ($\alpha$) is an average of the plurality of bias corrected first set of gyroscope data. For every data sample ($S_i$) from the plurality of data samples with i>m+k−1, a compound simultaneous rotation angle can be calculated as follows:

$$\alpha_i = \sqrt{(\theta_i^x)^2 + (\theta_i^y)^2 + (\theta_i^z)^2} \text{ where,} \quad (5)$$

$$\theta_i^x = \left(\left(\frac{X_i + X_{i-1}}{2}\right) \times (t_i - t_{i-1})\right)^2$$

$$\theta_i^y = \left(\left(\frac{Y_i + Y_{i-1}}{2}\right) \times (t_i - t_{i-1})\right)^2$$

$$\theta_i^z = \left(\left(\frac{Z_i + Z_{i-1}}{2}\right) \times (t_i - t_{i-1})\right)^2$$

Hence, for all the plurality of data samples are calculated as product of average of bias-corrected first set of gyroscope data of the respective axis for $S_i$ and $S_{i+1}$ and the difference of time between $S_i$ and $S_{i+1}$ in the first pre-defined window.

After computing the set of bias correction parameters (includes a plurality of bias corrected first set of gyroscope data and a plurality of sample angles ($\alpha$)) the subject or the specialist who is assisting in the ROM computation can be provided feedback (audio/visual/tactile) to begin the rotation of the limb or the pre-defined rotation movement of the joint as explained in the further sections for computation of ROM. The feedback is automated and is provided by the system 100 upon sensing a completion of the pre-defined neutral position, wherein the completion of the pre-defined neutral position is sensed using a plurality of sensors based on a pre-defined time instance. The objective of the feedback is to alert the subject to start rotation at the point of receiving this feedback.

Referring to FIG. 3B, at step 306 of the method 300, a second set of gyroscope data is received from the subject using the wearable device 202. The second set of gyroscope data is associated with the joint rotation of the subject at the pre-defined rotation movement of the joint. The second set of gyroscope data is received at a pre-defined rotation movement of a joint of the subject.

In an embodiment, the pre-defined joint rotation movement of the subject is a pre-defined rotation of the joint of the subject where the ROM is computed. In an example scenario, considering an arm joint movement, the pre-defined rotation movement includes an upward and a downward movement of the arm joint. The FIG. 5A illustrates a side view of a subject performing a shoulder flexion by moving arm joint upwards. The FIG. 5A illustrates a side view of a subject bringing the arm down after performing a shoulder flexion.

At step 308 of the method 300, a bias corrected second set of gyroscope data is obtained for the second set of gyroscope data at the bias correction module 204. The bias corrected second set of gyroscope data is obtained using the set of bias correction parameters.

In an embodiment, all the second set of gyroscope data lying between, i>m+k−1, plurality of bias corrected second set of gyroscope data is computed as follows:

$$S_i = \{t_i, X_i, Y_i, Z_i\} \quad (6)$$

where,
$X_i = x_i - B_x$,
$Y_i = y_i - B_y$, and
$Z_i = z_i - B_z$.

Hence the plurality of bias corrected second set of gyroscope data is computed for the second set of gyroscope data bias correction for a particular data sample can be performed by subtracting the calculated static bias parameter from the actual raw sample value.

At step 310 of the method 300, the bias corrected second set of gyroscope data as one of a valid session or an invalid session in the validation module 206. The validation is performed based on a deviation angle ($\phi$) and a pre-defined delta angle ($\delta$). The deviation angle is computed using a reference rotation axis ($\vec{R}$) and a rotation axis ($\vec{V}$). The reference rotation axis ($\vec{R}$) and the rotation axis ($\vec{V}$) is estimated in a second pre-defined window based on the plurality of sample angles ($\alpha$).

In an embodiment, the second pre-defined window is defined based on the plurality of bias corrected second set of gyroscope data and a second pre-defined threshold parameter ($C_U$). The second pre-defined threshold parameter ($C_U$) is a predetermined threshold and can be altered as per the requirement of the subject. A typical value for the $C_U$ can be 0.03 degrees at a sampling rate of 200 samples per second. The typical value of 0.03 for the second pre-defined threshold parameter ($C_U$) at 200 hz sampling rate implies a speed of 6 degrees/second, which marks the speed at which the ongoing rotational motion is expected to represent the actual motion pertaining to the ROM estimation, and not owing to the sensor noise or any other undesired source. The second pre-defined threshold parameter ($C_U$) can be adjusted as per the requirement of the specialist, which lower values set for slower rotational speed during the ROM estimation session.

The deviation angle ($\phi$) is computed using the reference rotation axis ($\vec{R}$) and the rotation axis ($\vec{V}$). The reference rotation axis ($\vec{R}$) and the rotation axis ($\vec{V}$) is computed at the second pre-defined window based on a plurality of sample angles ($\alpha$). Let the set of all the samples in the second pre-defined window ($W_a$) for which the value a is greater than $C_U$ be represented as K. Hence, K is expressed as shown below:

$$K=\{S_i:(S_i \in W_a) \wedge (\alpha_i > C_U)\} \quad (7)$$

When the second pre-defined window ($W_a$) is encountered, the reference rotation axis about which the limb is being rotated which can be represented as:

$$\text{reference rotation axis } (\vec{R}) \text{ is } \vec{R}=r_x\hat{i}+r_y\hat{j}+r_z\hat{k}; \quad (8)$$

where,
$\hat{i}$, $\hat{j}$ and $\hat{k}$ are unit vectors in X-axis, Y-axis and Z-axis respectively of the plurality of bias corrected second data samples;

$$r_x = \frac{\Sigma_K X_i}{|K|}, r_y = \frac{\Sigma_K Y_i}{|K|}, r_x = \frac{\Sigma_K Z_i}{|K|} \quad (9)$$

Hence, $r_x$, $r_y$, and $r_y$ are the average values of X, Y and Z components of all the samples which belong to the set K.

The rotation axis ($\vec{V}$) is represented as an axis vector and is defined for every data sample $S_i$ (for all i>k) in the following manner:

$$\text{rotation axis } (\vec{V}) \text{ is } \vec{V}=\theta_i^x\hat{i}+\theta_i^y\hat{j}+\theta_i^z\hat{k} \quad (10)$$

wherein,
$\theta_i^x\hat{i}$ represents an angle rotated by the wearable device during $i^{th}$ data sample along x—axis of the gyroscope,
$\theta_i^y\hat{i}$ represents an angle rotated by the wearable device during $i^{th}$ data sample along y—axis of the gyroscope, and
$\theta_i^z\hat{i}$ represents an angle rotated by the wearable device during $i^{th}$ data sample along z—of the gyroscope The deviation angle is computed using a reference rotation axis ($\vec{R}$) and a rotation axis ($\vec{V}$), as expressed below:

$$\phi_i = \cos^{-1}\left(\frac{\vec{R}.\vec{V}}{|\vec{R}||\vec{V}|}\right) \quad (11)$$

Hence, the deviation angle is the angle between the reference rotation axis and the rotation axis.

At step 312 of the method 300, the range of motion (ROM) of a joint and the set of ROM parameters is computed in the ROM module 208 if the validated bias corrected second set of gyroscope data is the valid session.

The range of motion (ROM) of a joint and a set of ROM parameters is computed in the ROM module 208 using the modules within the ROM module 208 that includes a real-time cumulative angle module 210, a ROM computation module 212, a ROM parameter module 214.

At step 312A of the method 300, a real-time cumulative angle ($C_i$) is computed in the real-time cumulative angle computation module 210 of the ROM module 208. The real-time cumulative angle ($C_i$) is computed for each of the plurality of bias corrected second set of gyroscope data to obtain a plurality of the real-time cumulative angle (C) The real-time cumulative angle ($C_i$) is computed using the plurality of sample angles ($\alpha$), the deviation angle ($\phi$) and the pre-defined delta angle ($\delta$).

In an embodiment, the real-time cumulative angle ($C_i$) at every data sample $S_i$ can be calculated using the plurality of sample angles ($\alpha$), the deviation angle ($\phi$) and the pre-defined delta angle ($\delta$) as follows:

$$\text{If } \phi_i < \delta \text{ then } C_i = C_{i-1} + \alpha_i \quad (13)$$

$$\text{If } \phi_i > (2\pi - \delta) \text{ then } C_i = C_{i-1} - \alpha_i \quad (14)$$

else, declare that session is invalid

The equation (13) signifies the case when the limb is rotated along an axis in the direction same as that the initial movement, using which the reference rotation axis ($\vec{R}$) is calculated using equation (9) and (10). Equation (14) signifies the case when the limb is rotated along an axis which is opposite in direction to the reference rotation axis ($\vec{R}$). Any measurement session involves rotating the limb in two directions with an exactly opposite angular trajectory in a plane for a complete range of motion measurement. For e.g., during the shoulder flexion/extension range of motion calculation, the flexion is performed by moving the arm upwards from neutral/normal position as illustrated in FIG. 5A as a first rotation, during which the validity may be executed using equation 13. The arm can be brought back to neutral/normal position by retracing the angular trajectory and an extension may then be performed position as illustrated in FIG. 5A by continuing through the neutral/normal position, as a second rotation for which, the validity may be executed using equation (14).

Figure 6A:
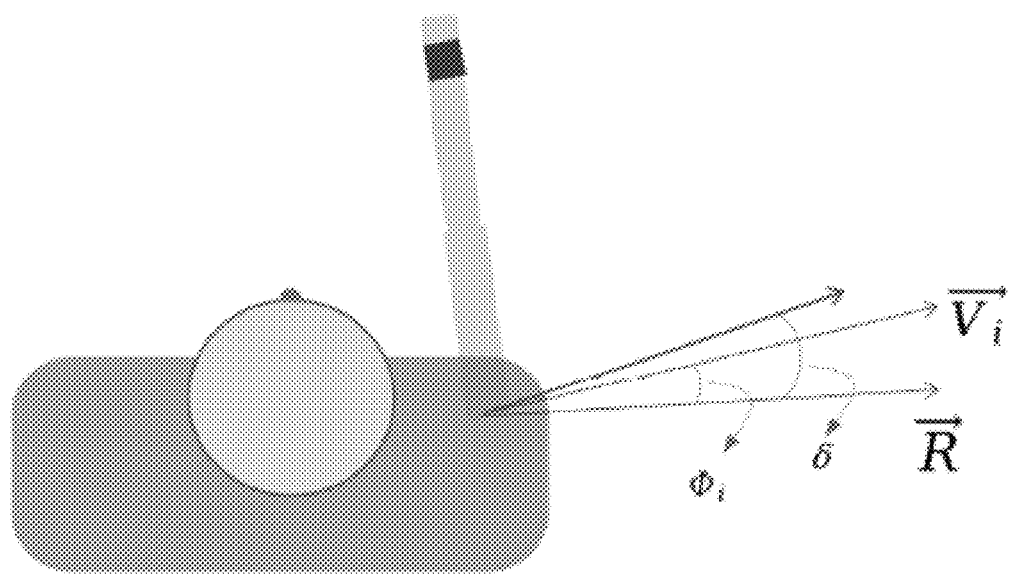
FIG. 6A illustrates a top view of a subject performing the pre-defined rotation movement of FIG. 5A, by an upward movement of the arm joint, signifying a valid session as per a deviation angle ($\phi$) and a pre-defined delta angle ($\delta$) in accordance with some embodiments of the present disclosure.

As an example, when a range of motion of elbow joint is being estimated for internal/external rotational action, the forearm may be rotated away from the body first, during which the calculation of cumulative angles will fall in the category of equation (13) as illustrated in FIG. 6A as a top view of a subject performing the pre-defined rotation movement of FIG. 5A, by an upward movement of the arm joint. the cumulative angles in FIG. 6A is computed by adding the angles from the plurality of sample angles ($\alpha$), signifying a valid session as per a deviation angle ($\phi$) and a pre-defined delta angle ($\delta$).

Figure 6B:
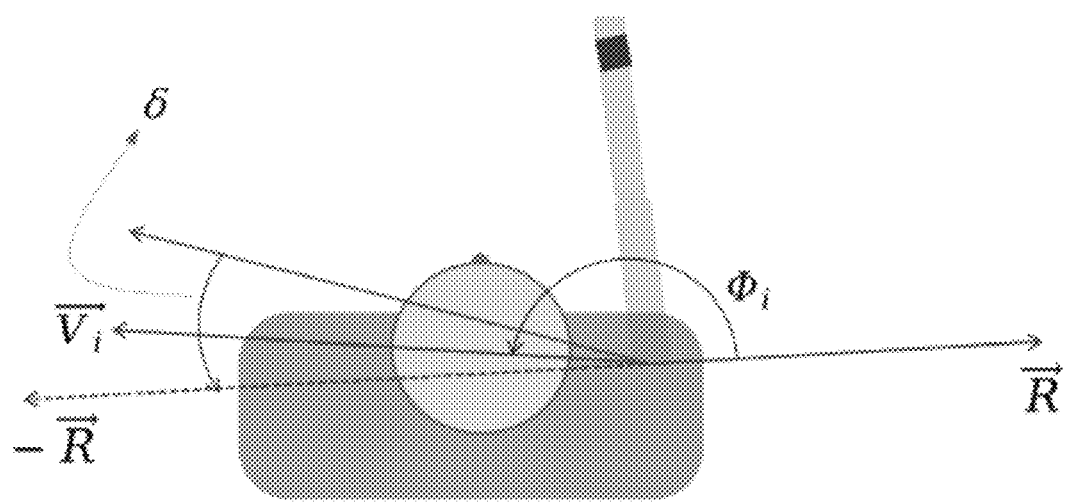
FIG. 6B illustrates a top view of a subject performing the pre-defined rotation movement of FIG. 5B, by downward movement of the arm joint, signifying a valid session as per a deviation angle ($\phi$) and a pre-defined delta angle ($\delta$) in accordance with some embodiments of the present disclosure.

Further, consider a opposite movement compared to movement of FIG. 5A, as shown in FIG. 6B, wherein the FIG. 6B illustrates a top view of a subject performing the pre-defined rotation movement of FIG. 5B, by downward movement of the arm joint, the cumulative angles are computed by subtracting the angles from the plurality of sample angles ($\alpha$), signifying a valid session as per a deviation angle ($\phi$) and a pre-defined delta angle ($\delta$) in accordance with some embodiments of the present disclosure. during which the calculation of cumulative angles will fall in the category of (14) as illustrated in FIG. 6B.

Figure 6C:
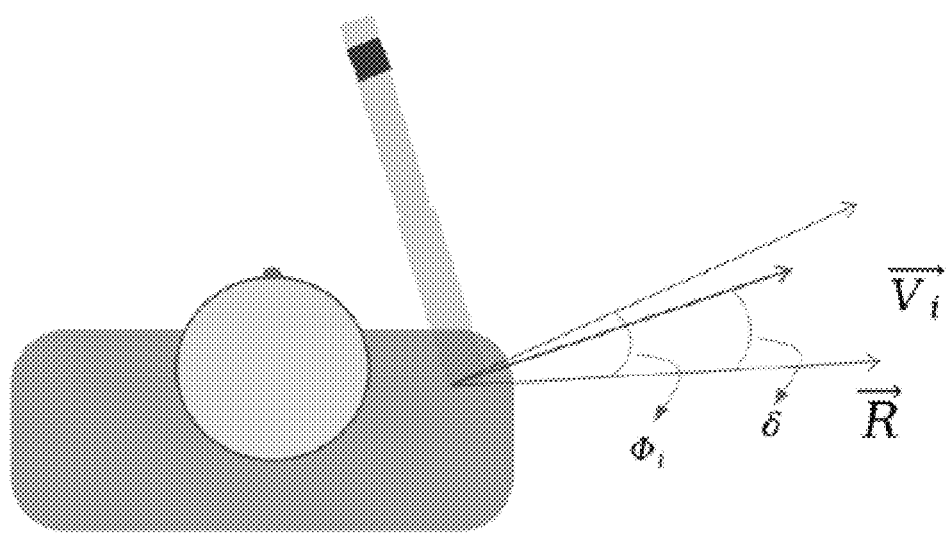
FIG. 6C illustrates a top view of a subject performing the pre-defined rotation movement of FIG. 5A, by an upward movement of the arm joint, signifying an invalid session as per a deviation angle ($\phi$) and a pre-defined delta angle ($\delta$) in accordance with some embodiments of the present disclosure.

Hence in FIG. 6A and FIG. 6B, with reference to equations (13, 14), the pre-defined parameter $\delta$ is used to ensure that the rotational movement happens approximately along the same axis (the reference axis). If any sample is encountered which satisfies neither Equation (13) nor equation (14), then the session is deemed to be in-valid and the subject can be instructed to restart the measurement session as illustrated in FIG. 6C, wherein, the FIG. 6C illustrates a top view of a subject performing the pre-defined rotation movement of FIG. 5A, by an upward movement of the arm joint. In the FIG. 6C, wherein a situation when the instantaneous axis of rotation, $V_i$ makes and angle with the reference axis of rotation, R which is out of threshold limits for the session to be a valid session signifying an invalid session as per a deviation angle ($\phi$) and a pre-defined delta angle ($\delta$).

At step 312B of the method 300, the joint ROM is computed in the ROM computation module 212 of the ROM module 208. The joint ROM is computed using the plurality of real-time cumulative angle (C), wherein the ROM is computed using a minimum real-time cumulative angle ($R_{min}$) and a maximum real-time cumulative angle ($R_{max}$) from the plurality of real-time cumulative angle (C).

In an embodiment, range of motion comprises of two numbers denoting the minimum ($R_{min}$) and maximum ($R_{max}$) angle that the subject's limb has rotated by during the whole session and can be calculated as follows:

$$R_{min} = \min\{C_i \forall i > m+k-1\} \quad (15)$$

$$R_{max} = \max\{C_i \forall i > m+k-1\} \quad (16)$$

At step 312C of the method 300, the set of ROM parameters is computed in the ROM parameter computation module 214 of the ROM module 208. The set of ROM parameters includes a speed of rotation ($\omega$), and a session validity score ($\lambda$) using the plurality of sample angles ($\alpha$), a pre-defined delta angle ($\delta$) and the deviation angle ($\phi$).

In an embodiment, the speed of rotation ($\omega$) is the rotational speed in all the three axes of the gyroscope, hence the compounded speed of rotation of the limb can be calculated in real time for every data sample $S_i$ $$\omega_i = \frac{\alpha_i}{t_i - t_{i-1}} \quad (17)$$

A session validity score ($\lambda$) score is calculated for every sample which depicts how closely the requirements of equations 13 and 14 are satisfied during the session.

For first motion (forward direction of movement of joint) during the range of motion calculation session valid session equation 13), the session validity score ($\lambda_i$), which is less than or equal to 1 can be calculated as follows:

$$\lambda_i = 1 - \frac{\phi_i}{\delta}; \quad (18)$$

denotes significant deviation from the reference axis of rotation during first motion.

The session validity score ($\lambda$) obtained closer to 1 denoting no deviation from the reference axis of rotation during the first motion. The session validity score ($\lambda$) score decreases to 0 and below if the $\phi_i$ becomes equal to or more than the pre-defined angle delta ($\delta$), which denotes significant deviation from the reference axis of rotation during first motion For second motion during the range of motion calculation session (valid session equation 14—opposite direction from the forward direction), a score between 0 and 1 can be calculated as follows for every data sample $S_i$:

$$\lambda_i = 1 - \frac{2\pi - \phi_i}{\delta}; \quad (19)$$

which denotes significant deviation from the negative of reference axis of rotation during second motion.

The session validity score ($\lambda$) decreases to 0 and below if ($2\pi - \phi_i$) becomes equal to or more than the pre-defined angle delta ($\delta$), which denotes significant deviation from the negative of reference axis of rotation during second motion.

Thus, the range of motion (ROM) of a joint and the set of ROM parameters computed in the ROM module 208 is displayed on the I/O interface(s) 106 or in the wearable device 202 based on the subject's requirement.

EXPERIMENTAL RESULTS

An experiment has been conducted with a subject wearing smart wristwatch with an embedded gyroscope, which transfers the data wirelessly to a computer. As the subject rotates the joint, the ROM is estimated using the disclosed for real time analysis of ROM. The estimation of ROM includes computing a real-time cumulative angle, the joint ROM using the plurality of real-time cumulative angle and finally computing the set of ROM parameters.

Figure 7A:
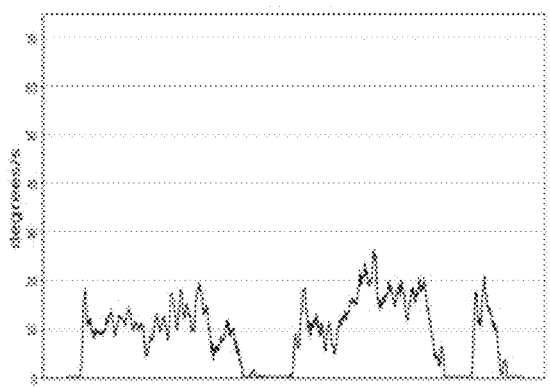
FIG. 7A illustrates a graph for the speed of rotation during the ROM analysis in accordance with some embodiments of the present disclosure.
Figure 7B:
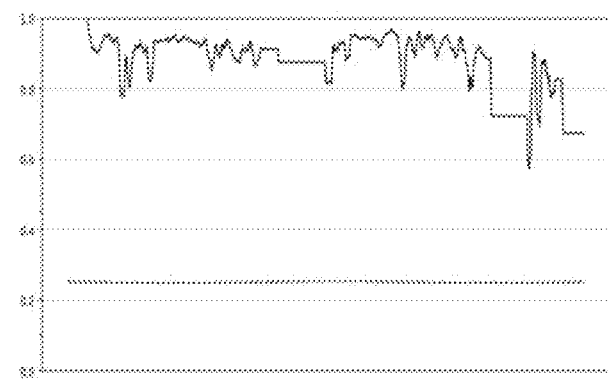
FIG. 7B illustrates a graph for the session validity score during the ROM analysis in accordance with some embodiments of the present disclosure.
Figure 7C:
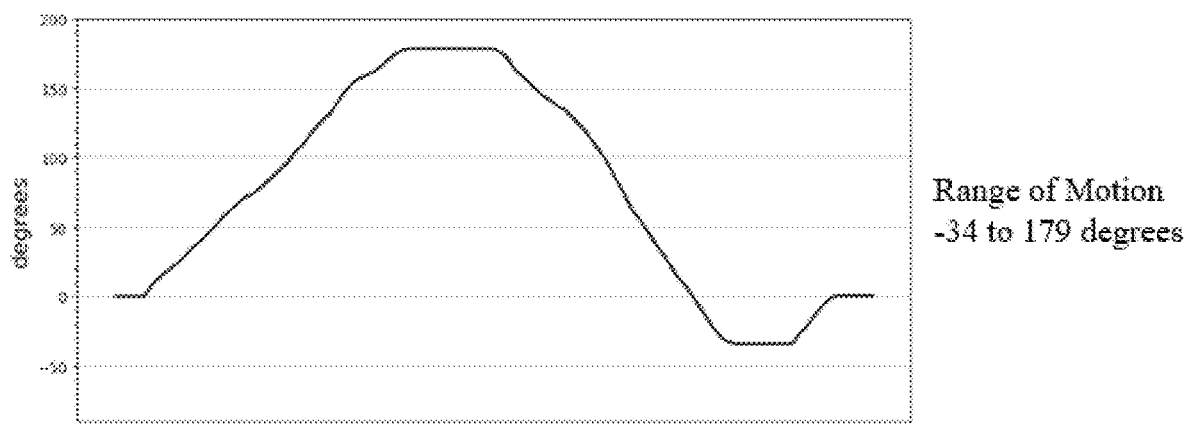
FIG. 7C illustrates a graph for the real-time cumulative angle during the ROM analysis in accordance with some embodiments of the present disclosure.

The results are illustrated in FIG. 7A to FIG. 7C. The FIG. 7A illustrates a real-time graph for the speed of rotation during the ROM analysis, wherein it can be inferred that speed of rotation can initially be seen rising during the first motion, and then coming back to zero before rising again for the second motion and then coming back to zero again. Further, the FIG. 7B illustrates a real-time graph for the session validity score during the ROM analysis, where since the session validity score can be seen to be closer to 1 denoting a valid session. The FIG. 7C illustrates a real-time graph for the real-time cumulative angle during the ROM analysis.

From the FIG. 7C, it can be inferred that the real-time cumulative angle can be seen rising initially to about 179 degrees marking the first rotation of the session, followed by fall in the cumulative angle marking the subject bringing back the limb to the neutral position, followed by the angle going in the negative direction till about −34 degrees marking the second rotation of the session, followed by bringing the limb back to the neutral position where the cumulative angle comes back to zero.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein provide a solution analysis of range of motion (ROM). The existing techniques for ROM fail for measurements made in certain planes and are not very effective for ROM measurements for extremely slow and very fast movements. The disclosed provides a real time analysis of ROM based on computation of range of motion (ROM) of a joint and a set of ROM parameters using a gyroscope. The gyroscope collects data from a subject at pre-defined neutral position of the subject as well as a pre-defined rotation movement of a joint of the subject. The received data is corrected for bias and processed at real time to analyze the ROM by computing range of motion (ROM) of a joint and a set of ROM parameters.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method for real time analysis of range of motion (ROM) comprising:

receiving a first set of gyroscope data from a subject, via one or more hardware processors, using a wearable device at a pre-defined neutral position of the subject, wherein the first set of gyroscope data is associated with a joint rotation of the subject at the pre-defined neutral position of the subject, wherein the first set of gyroscope data is processed for computation of the ROM within the wearable device;

computing a set of bias correction parameters from the first set of gyroscope data using a static bias parameter, via the one or more hardware processors, wherein the static bias parameter is computed from the first set of gyroscope data in a first pre-defined window and the set of bias correction parameters includes a plurality of bias corrected first set of gyroscope data and a plurality of sample angles ($\alpha$);

communicating an automated feedback to the subject to begin a pre-defined rotation movement of a joint of the subject for computation of the ROM, wherein the feedback is communicated upon sensing a completion of the pre-defined neutral position of the subject, wherein the completion of the pre-defined neutral position of the subject is sensed using a plurality of sensors based on a pre-defined time instance, wherein the feedback is communicated to alert the subject to start the rotation at a point of receiving the feedback, and wherein the feedback comprises at least one of audio, visual and tactile;

receiving a second set of gyroscope data from the subject, via the one or more hardware processors, using the wearable device at the pre-defined rotation movement of the joint of the subject, wherein the second set of gyroscope data is associated with the joint rotation of the subject at the pre-defined rotation movement of the joint;

obtaining a bias corrected second set of gyroscope data for the second set of gyroscope data, via the one or more hardware processors, using the set of bias correction parameters;

validating the bias corrected second set of gyroscope data as one of a valid session or an invalid session, via the one or more hardware processors, based on a deviation angle ($\varphi$) and a pre-defined delta angle ($\delta$), wherein the deviation angle is computed using a reference rotation axis ($\vec{R}$) and a rotation axis ($\vec{V}$), where the reference rotation axis and the rotation axis is estimated in a second pre-defined window based on the plurality of sample angles ($\alpha$);

computing the range of motion (ROM) of the joint and a set of ROM parameters, via one or more hardware processors, if the validated bias corrected second set of gyroscope data is the valid session, wherein the computing the ROM comprises:

computing a real-time cumulative angle ($C_i$) for each of the plurality of bias corrected second set of gyroscope data to obtain a plurality of the real-time cumulative angle (C) using the plurality of sample angles ($\alpha$), the deviation angle ($\phi$) and the pre-defined delta angle ($\delta$);

computing the joint ROM using the plurality of real-time cumulative angle (C), wherein the ROM is computed using a minimum real-time cumulative angle (C) and a maximum real-time cumulative angle (C) from the plurality of real-time cumulative angle (C); and computing the set of ROM parameters, wherein the set of ROM parameters includes a speed of rotation ($\omega$), and a session validity score ($\lambda$) using the plurality of sample angles ($\alpha$), the pre-defined delta angle ($\delta$) and the deviation angle ($\phi$), wherein the speed of rotation ($\omega$) is a rotational speed in all three axes of the wearable device and the speed of rotation of a limb is calculated in real time for each data sample; and displaying in real time the computated ROM of the joint and the set of ROM parameters on the wearable device.

2. The method according to claim 1, further comprising declaring the session as invalid and requesting for second set of gyroscope data from the subject to restate a ROM measurement session, if the validated second set of gyroscope data is the invalid session.

3. The method according to claim 1, wherein the wearable device comprises a gyroscope, the pre-defined neutral position of the subject is the neutral position of the subject from where the range of motion (ROM) calculations start and the pre-defined joint rotation movement of the subject is a pre-defined rotation of the joint of the subject where the ROM is computed, wherein the pre-defined rotation of the joint of the subject includes an upward movement of the joint and a downward movement of the joint.

4. The method according to claim 1, wherein the joint ROM is calculated for a bi-directional rotational movement of joints of the subject, wherein the bi-directional rotational movement of joints comprise of limbs movement including an abduction-adduction, an extension-flexion and an internal-external rotation.

5. The method according to claim 1, wherein the process of computing a set of bias correction parameters comprises:
computing the static bias parameter in the first pre-defined window, wherein the static bias parameter is computed as a mean of the first set of gyroscope data taken independently in all three axes of the wearable device;
computing the plurality of bias corrected first set of gyroscope data for the first set of gyroscope data using the static bias parameter; and
computing a plurality of sample angles ($\alpha$) for the plurality of bias corrected first set of gyroscope data, wherein the plurality of sample angles is an average of the plurality of bias corrected first set of gyroscope data, where a sample angle is computed for each of the bias corrected first set of gyroscope data from the plurality of bias corrected first set of gyroscope data.

6. The method according to claim 1, wherein the first pre-defined window is defined based on a standard deviation of the first set of gyroscope data and a first predefined threshold ($C_L$) on the standard deviation of the first set of gyroscope data.

7. The method according to claim 1, wherein the second pre-defined window is defined based on the plurality of bias corrected second set of gyroscope data and a second pre-defined threshold parameter ($C_U$), wherein the second pre-defined threshold parameter is adjusted to lower values set for slower rotational speed during a ROM measurement session.

8. The method according to claim 1, wherein the deviation angle ($\phi$) is computed using the reference rotation axis ($\vec{R}$) and the rotation axis ($\vec{V}$), as expressed below:

$$\phi_i = \cos^{-1}\left(\frac{\vec{R}.\vec{V}}{|\vec{R}||\vec{V}|}\right)$$

where, the in the reference rotation axis ($\vec{R}$) and the rotation axis ($\vec{V}$) is computed at the second pre-defined window based on a plurality of sample angles ($\alpha$) as shown below:

reference rotation axis ($\vec{R}$) is $\vec{R}=r_x\hat{i}+r_y\hat{j}+r_z\hat{k}$; and and a rotation axis ($\vec{V}$) is $\vec{V}=\theta_i^x\hat{i}+\theta_i^y\hat{j}+\theta_i^z\hat{k}$;

wherein, $\hat{i}$, $\hat{j}$ and $\hat{k}$ are unit vectors in X-axis, Y-axis and Z-axis respectively of the plurality of bias corrected first data samples, $$r_x = \frac{\Sigma_K X_i}{|K|}, r_y = \frac{\Sigma_K Y_i}{|K|}, r_z = \frac{\Sigma_K Z_i}{|K|}$$

wherein $r_x$, $r_y$, and $r_y$ are the average values of X, Y and Z components of all the samples which belong to the set K.

9. The method according to claim 1, wherein the speed of rotation ($\omega$) is computed using the plurality of sample angles ($\alpha$), and a session validity score ($\lambda$) is computed using the pre-defined delta angle ($\delta$) and the deviation angle ($\phi$) and is expressed as shown below:

a speed of rotation ($\omega$) is $$(\omega_i) = \frac{\alpha_i}{t_i - t_{i-1}}$$

and a session validity score ($\lambda$) is defined as;

$$\lambda_i = 1 - \frac{\phi_i}{\delta}$$

for forward movement, and $$\lambda_i = 1 - \frac{2\pi - \phi_i}{\delta}$$

for the direction opposite to forward movement.

10. A system, comprising:
a memory storing instructions;
one or more communication interfaces; and
one or more hardware processors coupled to the memory via the one or more communication interfaces, wherein the one or more hardware processors are configured by the instructions to:
receive a first set of gyroscope data from a subject, via one or more hardware processors, using a wearable device at a pre-defined neutral position of the subject, wherein the first set of gyroscope data is associated with a joint rotation of the subject at the pre-defined neutral position of the subject, wherein the first set of gyroscope data is processed for computation of the ROM within the wearable device;

compute a set of bias correction parameters from the first set of gyroscope data using a static bias parameter, via the one or more hardware processors, wherein the static bias parameter is computed from the first set of gyroscope data in a first pre-defined window and the set of bias correction parameters includes a plurality of bias corrected first set of gyroscope data and a plurality of sample angles ($\alpha$);

communicate an automated feedback generated by the system to the subject to begin a pre-defined rotation movement of a joint of the subject for computation of the ROM, wherein the feedback is communicated upon sensing a completion of the pre-defined neutral position of the subject, wherein the completion of the pre-defined neutral position of the subject is sensed using a plurality of sensors based on a pre-defined time instance, wherein the feedback is communicated to alert the subject to start the rotation at a point of receiving the feedback, and wherein the feedback comprises at least one of audio, visual and tactile;

receive a second set of gyroscope data from the subject, via the one or more hardware processors, using the wearable device at the pre-defined rotation movement of the joint of the subject, wherein the second set of gyroscope data is associated with the joint rotation of the subject at the pre-defined rotation movement of the joint;

obtain a bias corrected second set of gyroscope data for the second set of gyroscope data, via the one or more hardware processors, using the set of bias correction parameters;

validate the bias corrected second set of gyroscope data as one of a valid session or an invalid session, via the one or more hardware processors, based on a deviation angle ($\phi$) and a pre-defined delta angle ($\delta$), wherein the deviation angle is computed using a reference rotation axis ($\vec{R}$) and a rotation axis ($\vec{V}$), where the reference rotation axis and the rotation axis is estimated in a second pre-defined window based on the plurality of sample angles ($\alpha$);

compute the range of motion (ROM) of the joint and a set of ROM parameters, via one or more hardware processors, if the validated bias corrected second set of gyroscope data is the valid session, wherein the computing the ROM comprises:
  computing a real-time cumulative angle ($C_i$) for each of the plurality of bias corrected second set of gyroscope data to obtain a plurality of the real-time cumulative angle (C) using the plurality of sample angles ($\alpha$), the deviation angle ($\phi$) and the pre-defined delta angle ($\delta$);
  computing the joint ROM using the plurality of real-time cumulative angle (C), wherein the ROM is computed using a minimum real-time cumulative angle (C) and a maximum real-time cumulative angle (C) from the plurality of real-time cumulative angle (C); and
  computing the set of ROM parameters, wherein the set of ROM parameters includes a speed of rotation ($\omega$), and a session validity score ($\lambda$) using the plurality of sample angles ($\alpha$), the pre-defined delta angle ($\delta$) and the deviation angle ($\phi$), wherein the speed of rotation ($\omega$) is a rotational speed in all three axes of the wearable device and the speed of rotation of a limb is calculated in real time for each data sample; and display in real time the computed ROM of the joint and the set of ROM parameters on the wearable device.

11. The system according to claim 10, wherein the one or more hardware processors are configured by the instructions to validate second set of gyroscope data, wherein when the second set of gyroscope data is validated as the invalid session, then the session is declared as invalid and the second set of gyroscope data is requested again from the subject to restart a ROM measurement session.

12. The system according to claim 10, wherein the one or more hardware processors are configured by the instructions to calculate the joint ROM for a bi-directional rotational movement of joints of the subject, wherein the bi-directional rotational movement of joints comprise of limbs movement including an abduction-adduction, an extension-flexion and an internal-external rotation.

13. The system according to claim 10, wherein the one or more hardware processors are configured by the instructions to compute a set of bias correction parameters, comprising:
  computing the static bias parameter in the first pre-defined window, wherein the static bias parameter is computed as a mean of the first set of gyroscope data taken independently in all three axes of the wearable device;
  computing the plurality of bias corrected first set of gyroscope data for the first set of gyroscope data using the static bias parameter; and
  computing a plurality of sample angles ($\alpha$) for the plurality of bias corrected first set of gyroscope data, wherein the plurality of sample angles is an average of the plurality of bias corrected first set of gyroscope data, where a sample angle is computed for each of the bias corrected first set of gyroscope data from the plurality of bias corrected first set of gyroscope data.

14. The system according to claim 10, wherein the one or more hardware processors are configured by the instructions to compute the deviation angle ($\phi$) using the reference rotation axis ($\vec{R}$) and the rotation axis ($\hat{V}$), as expressed below:

$$\phi_i = \cos^{-1}\left(\frac{\vec{R}.\vec{V}_i}{|\vec{R}||\vec{V}_i|}\right)$$

where, the in the reference rotation axis ($\vec{R}$) and the rotation axis ($\vec{V}$) is computed at the second pre-defined window based on a plurality of sample angles ($\alpha$) as shown below:

reference rotation axis ($\vec{R}$) is $\vec{R}=r_x\hat{i}+r_y\hat{j}+r_z\hat{k}$; and and a rotation axis ($\vec{V}$) is $\vec{V}=\theta_i^x\hat{i}+\theta_i^y\hat{j}+\theta_i^z\hat{k}$;

wherein,
  $\hat{i}, \hat{j}$ and $\hat{k}$ are unit vectors in X-axis, Y-axis and Z-axis respectively of the plurality of bias corrected first data samples, $$r_x = \frac{\Sigma_K X_i}{|K|}, r_y = \frac{\Sigma_K Y_i}{|K|}, r_z = \frac{\Sigma_K Z_i}{|K|}$$

wherein $r_x$, $r_y$, and $r_y$ are the average values of X, Y and Z components of all the samples which belong to the set K.

15. The system of claim 10, wherein the one or more hardware processors are configured by the instructions to compute the speed of rotation (ω) using the plurality of sample angles (α), and a session validity score (λ) is computed using the pre-defined delta angle (δ) and the deviation angle (φ) and is expressed as shown below:

a speed of rotation (ω) is $$(\omega_i) = \frac{\alpha_i}{t_i - t_{i-1}}$$

a session validity score (λ) is defined as:

$$\lambda_i = 1 - \frac{\phi_i}{\delta}$$

for forward movement, and $$\lambda_i = 1 - \frac{2\pi - \phi_i}{\delta}$$

for the direction opposite to forward movement.

16. One or more non-transitory machine-readable information storage mediums comprising one or more instructions which when executed by one or more hardware processors cause:

receive a first set of gyroscope data from a subject, via one or more hardware processors, using a wearable device at a pre-defined neutral position of the subject, wherein the first set of gyroscope data is associated with a joint rotation of the subject at the pre-defined neutral position of the subject, wherein the first set of gyroscope data is processed for computation of the ROM within the wearable device;

compute a set of bias correction parameters from the first set of gyroscope data using a static bias parameter, via the one or more hardware processors, wherein the static bias parameter is computed from the first set of gyroscope data in a first pre-defined window and the set of bias correction parameters includes a plurality of bias corrected first set of gyroscope data and a plurality of sample angles (α);

communicate an automated feedback to the subject to begin a pre-defined rotation movement of a joint of the subject for computation of the ROM, wherein the feedback is communicated upon sensing a completion of the pre-defined neutral position of the subject, wherein the completion of the pre-defined neutral position of the subject is sensed using a plurality of sensors based on a pre-defined time instance, wherein the feedback is communicated to alert the subject to start the rotation at a point of receiving the feedback, and wherein the feedback comprises at least one of audio, visual and tactile;

receive a second set of gyroscope data from the subject, via the one or more hardware processors, using the wearable device at the pre-defined rotation movement of the joint of the subject, wherein the second set of gyroscope data is associated with the joint rotation of the subject at the pre-defined rotation movement of the joint;

obtain a bias corrected second set of gyroscope data for the second set of gyroscope data, via the one or more hardware processors, using the set of bias correction parameters;

validate the bias corrected second set of gyroscope data as one of a valid session or an invalid session, via the one or more hardware processors, based on a deviation angle (φ) and a pre-defined delta angle (δ), wherein the deviation angle is computed using a reference rotation axis ($\vec{R}$) and a rotation axis ($\vec{V}$), where the reference rotation axis and the rotation axis is estimated in a second pre-defined window based on the plurality of sample angles (α); and compute the range of motion (ROM) of the joint and a set of ROM parameters, via one or more hardware processors, if the validated bias corrected second set of gyroscope data is the valid session, wherein the computing the ROM comprises:

computing a real-time cumulative angle ($C_i$) for each of the plurality of bias corrected second set of gyroscope data to obtain a plurality of the real-time cumulative angle (C) using the plurality of sample angles (α), the deviation angle (φ) and the pre-defined delta angle (δ);

computing the joint ROM using the plurality of real-time cumulative angle (C), wherein the ROM is computed using a minimum real-time cumulative angle (C) and a maximum real-time cumulative angle (C) from the plurality of real-time cumulative angle (C); and computing the set of ROM parameters, wherein the set of ROM parameters includes a speed of rotation (ω), and a session validity score (λ) using the plurality of sample angles (α), the pre-defined delta angle (δ) and the deviation angle (φ), wherein the speed of rotation (ω) is a rotational speed in all three axes of the wearable device and the speed of rotation of a limb is calculated in real time for each data sample; and display in real time the computated ROM of the joint and the set of ROM parameters on the wearable device.

17. The method according to claim 1, wherein the session validity score (λ) is less than or equal to 1 denotes significant deviation from a reference axis of the rotation during a forward direction of movement of the joint during the valid session, wherein the session validity score (λ) obtained closed to 1 denotes no deviation from the reference axis of the rotation during the forward direction of movement of the joint and the session validity score (λ) score decreases to 0 and below, if the deviation angle is equal to or more than the pre-defined angle delta (δ) to denote significant deviation from the reference axis of the rotation during the forward direction of movement of the joint, and wherein the session validity score (λ) between 0 and 1 denotes significant deviation from a negative of reference axis of the rotation during a direction opposite to the forward direction of movement of the joint and the session validity score (λ) decreases to 0 and below if ($2\pi - \phi_i$) is equal to or more than the pre-defined angle delta (δ) to denote significant deviation from the negative of reference axis of the rotation.

* * * * *